(12) United States Patent
Gordon et al.

(10) Patent No.: US 7,366,627 B2
(45) Date of Patent: Apr. 29, 2008

(54) METHOD FOR SATISFYING CERTIFICATION REQUIREMENTS AND VERIFYING THE INTEGRITY OF STRUCTURAL HEALTH MANAGEMENT SYSTEMS

(75) Inventors: Grant A. Gordon, Peoria, AZ (US); Nicholas J. Wilt, Glendale, AZ (US); Joseph J. Nutaro, Phoenix, AZ (US)

(73) Assignee: Honeywell International, Inc., Morristown, NJ (US)

( * ) Notice: Subject to any disclaimer, the term of this patent is extended or adjusted under 35 U.S.C. 154(b) by 335 days.

(21) Appl. No.: 11/142,038

(22) Filed: May 31, 2005

(65) Prior Publication Data
US 2006/0282297 A1  Dec. 14, 2006

(51) Int. Cl.
*G06F 19/00* (2006.01)
(52) U.S. Cl. .......................... 702/105; 702/85
(58) Field of Classification Search ............... 73/769; 702/85, 105
See application file for complete search history.

(56) References Cited

U.S. PATENT DOCUMENTS 4,480,480 A * 11/1984 Scott et al. ................... 73/769
6,006,163 A * 12/1999 Lichtenwalner et al. ...... 702/36
7,103,507 B2 * 9/2006 Gorinevsky et al. ........ 702/184

* cited by examiner

*Primary Examiner*—John Barlow
*Assistant Examiner*—Douglas N Washburn
(74) *Attorney, Agent, or Firm*—Ingrassia Fisher & Lorenz

(57) ABSTRACT

A method is disclosed wherein a plurality of sensors mounted on a structure, a baseline data set for each of the plurality of sensors and a calibration procedure verify the integrity of a structural health management system. Initially a baseline data set is established. Before performing the structural health assessment a calibration-in data set for each of the plurality of sensors is collected. The calibration-in data set is compared to the baseline data set for each sensor of the plurality of sensors. If the calibration-in data set and the baseline data set match then a structure characterization is performed. If the calibration-in data set and the baseline data set do not match, a calibration-out procedure is performed to generate a calibration-out data set. If the calibration-out data set and the calibration-in data sets match, then a determination is made that the structural health management system was working.

20 Claims, 3 Drawing Sheets

METHOD FOR SATISFYING CERTIFICATION REQUIREMENTS AND VERIFYING THE INTEGRITY OF STRUCTURAL HEALTH MANAGEMENT SYSTEMS

TECHNICAL FIELD

This invention relates to the field of structural health management and condition based maintenance for aircraft structures, and more particularly, to a method for satisfying certification requirements and verifying the integrity of structural health management systems.

BACKGROUND

Nondestructive testing is a procedure for determining the quality or characteristics of a structure without permanently altering the structure or the structure's properties. Examples include ultrasonic and radiographic inspection. In the air transport industry, nondestructive testing of aircraft components is done to insure the structural integrity of the aircraft. In typical nondestructive testing schemes, a certified inspector performs one or more nondestructive tests on the aircraft. This process may be repeated at regular intervals to monitor and manage the structural health of the aircraft by providing, if needed, appropriate repairs.

While this type of nondestructive testing scheme can be effective, it has several drawbacks. First, the tests are typically conducted by trained inspectors, which can incur significant costs and potential operational delays especially if the inspection is part of an unscheduled maintenance action. Second, to enable efficient analysis, such as trending to identify potential problems and monitor performance, accurate, and context sensitive methods capable of making repetitive objective comparison over time are sometimes used. This process may use detailed inspection data, including inspection method parameters, damage location, decision criteria, and material properties within the context of the local structural area being inspected. Current inspection approaches generally do not preserve these necessary components with sufficient detail or accuracy To resolve some of the above-noted drawbacks of current nondestructive schemes, other structural health management (SHM) schemes have been developed. In one structural health management technique, ultrasonic transducers are installed on the inside surface of the aircraft fuselage. The ultrasonic transducers are coupled to an onboard computer that is used to run nondestructive tests. This system allows nondestructive testing to be conducted without having an inspector bring equipment to the aircraft. The intent is to obtain real-time or on demand data from the sensors in order to detect various undesired conditions. In addition to the potential for improvements in performance, this system can reduce total operational costs by averting unscheduled maintenance, reducing the cost and number of potentially difficult inspections, and shifting line maintenance checks to base maintenance checks, while enhancing higher levels of aircraft availability.

Establishing a practical aircraft SHM system requires that the system achieve maintenance credit in an economically viable way while meeting the requirements of certifying agencies such as the Federal Aviation Administration (FAA) and Joint Aviation Authorities (JAA). There are two general aspects that need to be considered. The SHM system should be capable of achieving an airworthiness certification as part of an on-board system and should be capable of achieving approval as part of an airline maintenance program.

For each eligible aircraft that is registered in the United States, the FAA has the responsibility of issuing a Standard Airworthiness Certificate indicating that the FAA has determined the aircraft conforms to FAA-approved type design and is in a safe operating condition where appropriate. Various types of certificates and production approvals support the Standard Airworthiness Certificates. Any system used on commercial aircraft today must be certified that the system design meets certain safety requirements in performing its function. For example, Title 14 of the Code of Federal Regulations (CFR), Part 25, entitled "Airworthiness Standards: Transportation Category", specifies that equipment, systems and installations must be designed such that the occurrence of any failure condition that would prevent the continued safe flight and landing of the aircraft is extremely improbable. Various means of showing compliance with these requirements are discussed in supporting documents such as Advisory Circulars e.g. AC 25.1309-1A, (*System Design and Analysis, Advisory Circular*, FAA) and documents published by industry standards groups such as SAE ARP4761. For structural health management systems this entails providing information that the portion of the structure being monitored is flight worthy.

These safety requirements for functional integrity are often expressed as the probability of an undesired effect occurring. These probabilities require analysis of the system and are based in large part upon the failure rate of the electronic components and upon the configuration of the system. Using traditional avionics system approaches, one way to meet the functional integrity requirements are for the inspection system, e.g. sensors, conversion circuitry, and processors, to be involved in some sort of voting scheme. That is, two or more independent measurements and calculations are made and the results voted such that both must provide the same answer within some reasonable tolerance. Many versions of such schemes exist; however, they require redundant sensors and electronics plus voting components in order to obtain independence. In a structural health management system, which may include numerous sensors and related equipment, the duplication of components can make the system financially prohibitive.

The above description of the safety of the system addresses the components and their configuration within a structural health monitoring system architecture. Independently, the ability of the sensors and associated detection algorithms must themselves be proven capable of detecting the structural damage to the same probabilities as described above. This is similar to proving that aircraft control laws can control an aircraft; this must be proven independently of whether or not the architecture that implements the control laws is safe.

In addition to the oversight of design and manufacture of aircraft, certification agencies also manage aircraft safety through operation and maintenance rules for air carriers and repair facilities. Modern air transport vehicles are designed to meet continued structural airworthiness provided that the airframe structural integrity is maintained by an effective inspection and corrective maintenance program. As part of these requirements a maintenance facility must ensure that all test and inspection tools used to determine the airworthiness are calibrated to standards and at intervals acceptable to the FAA. What is needed is an SHM design and approach ensuring that the occurrence of any failure condition capable of preventing the continued safe flight and landing of the aircraft is extremely improbable.

BRIEF SUMMARY

In one embodiment of the present invention, a method for verifying the integrity of a structural health management system is disclosed. The structural health management system comprising a plurality of sensors mounted on a structure. In a first step, a baseline data set for each of the plurality of sensors is established, including single sensor responses and time-of-flight measurements between each of the plurality of sensors and neighboring sensor selected from the plurality of sensors. To begin structural health assessment a calibration-in data set for each of the plurality of sensors is collected. The calibration-in data set is compared to the baseline data set for each sensor of the plurality of sensors. If the calibration-in data set and the baseline data set match to within a certain criteria, structural characterization can proceed. After structural characterization measurements, a calibration-out procedure is performed to generate a calibration-out data set. The calibration-in and calibration-out data sets are compared to establish that they are similar to within certain criteria. The time between the calibration-in and calibration-out steps is sufficiently small that the probability of system failure during the intervening period of time can be shown to satisfy functional integrity requirements. It is then determined that the structural health management system was working during the structural characterization step.

In another embodiment, a method for verifying the integrity of a structural health management system is disclosed. In the method, the structural health management system is calibrated using a previous assessment of the structure as a reference. Next, the structure is interrogated to determine if there is damage. The structure is treated as an unknown. Then the structural health management system is recalibrated using the previous assessment of the structure as reference.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is discussed in an avionics embodiment, the teachings of the present invention are applicable to many different fields of endeavor.

Figure 1:
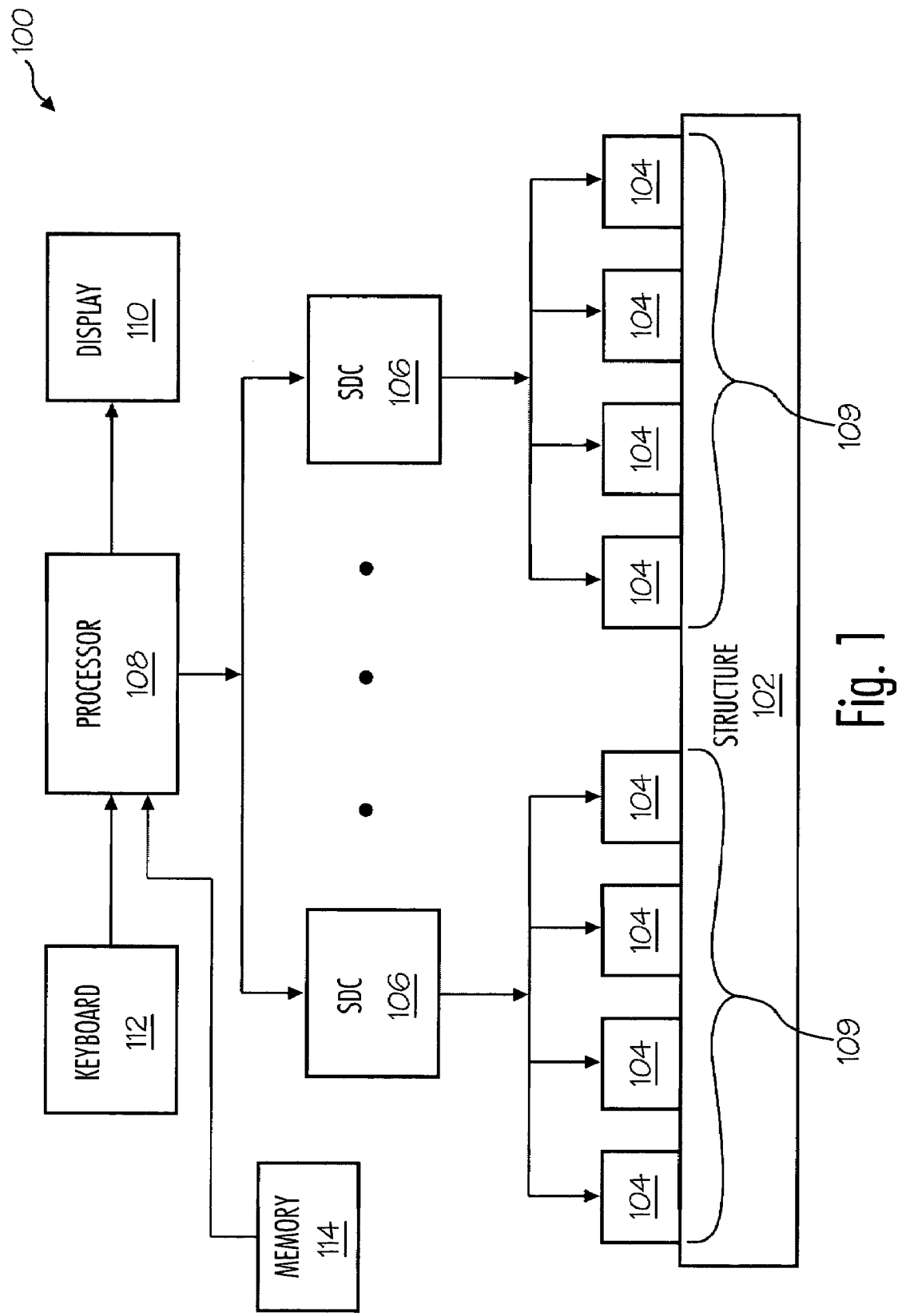
FIG. 1 illustrates an exemplary structural health management system in accordance with the teachings of the present invention.

FIG. 1 illustrates an exemplary structural health management system 100 in accordance with the teachings of the present invention. Structural health management system 100 includes a plurality of sensors 104 coupled to one or more sensor data collectors 106. Each sensor 104 is mounted to a structure 102 to be tested. The output of all the sensor data collectors 106 are provided as an input to at least one structural health management processor 108. Various inputs and outputs can be provided to structural health management processor 108. For example, processor 108 can be coupled to various input/output devices including a display 110, a keyboard 112 and the like. Processor 108 also is coupled to a memory 114.

Sensors 104 can be ultrasonic transducers that convert electrical signals into mechanical vibrations and mechanical vibrations into electrical signals. Typically, sensors 104 convert electrical signals into mechanical vibrations that propagate waves in the structure 102 to which the sensor 104 is coupled through elastic deformation (known as elastic waves). The propagated waves interact with various features within the structure 102 such as flaws or defects. The sensor 104 is also configured to receive transmitted and reflected waves, and to convert the mechanical vibrations caused by these received waves into electrical signals. These electrical signals are then analyzed to determine if there are any flaws or defects in the structure 102.

The amount of time it takes for a wave to travel between two sensed locations is known as a time-of-flight. In addition to the time-of-flight, signal amplitude, signal energy (area under the rectified voltage curve) and other features of an elastic wave received by sensor 104 can be used in models to predict state of the area traversed by the propagated elastic wave. Various features within the structure 102, such as fatigue cracks or other structural flaws, can be identified and located based on these features.

While many different designs for sensors 104 exist, in one embodiment, sensor 104 is a piezoelectric transducer. Piezoelectric transducers produce mechanical vibrations in response to an electric signal and produce electrical signals in response to mechanical vibrations. Typically, piezoelectric transducers use piezoelectric ceramics that can be engineered to produce different wave modes.

Sensor data collectors (SDCs) 106, in one embodiment of the present invention, collect data from the sensors 104 in the form of electrical signals and transmit the collected data to processor 108 for evaluation. In another embodiment, sensor data collectors 106 collect data and perform some analysis on the data prior to transmitting the data to the processor 108. By providing multiple sensor data collectors 106, if one sensor data collector 106 was inoperable, the structural health management system 100 would continue to operate. Additionally, in one embodiment, SDCs 106 receive data from multiple sensors 104 and provide a single high speed data output, which results in a reduction in the amount of wiring between the sensors 104 and the processor 108. While SDCs 106 are useful in reducing wiring and complexity, in one embodiment of the present invention, SDCs 106 are not used and data is routed directly from the sensors 104 to the processor 108.

Processor 108 receives data collected from the sensors 104, either directly or via SDCs 106. Processor 108 processes the received data to determine the health of structure 102. Processor 108 can support the execution of routines to verify the installation and determine the location of sensors 104. Processor 108 can be a commercial off the shelf processor and can include any components necessary to allow processor 108 to process the data. Processor 108 can couple to input/output devices such as the display 110, which may be a CRT or LCD display, which displays information to a user.

Memory 114 stores various programs executing on the processor 108. Also, memory 114 can provide storage of data used in the various programs executing on processor 108, including any needed databases, tables, listings and the like. Memory 114 can be any one of numerous types of memory used with processor 108. While memory 114 is shown as a single box in FIG. 1, memory 114 can represent two or more distinct memories, such as random access memory (RAM) and magnetic storage such as, for example, a hard drive.

Structure 102 can be any one of numerous types of material of interest to be tested. In one exemplary embodiment, structure 102 is a plate-like composite material such as the material used to form modern aircraft skin.

Figure 2:
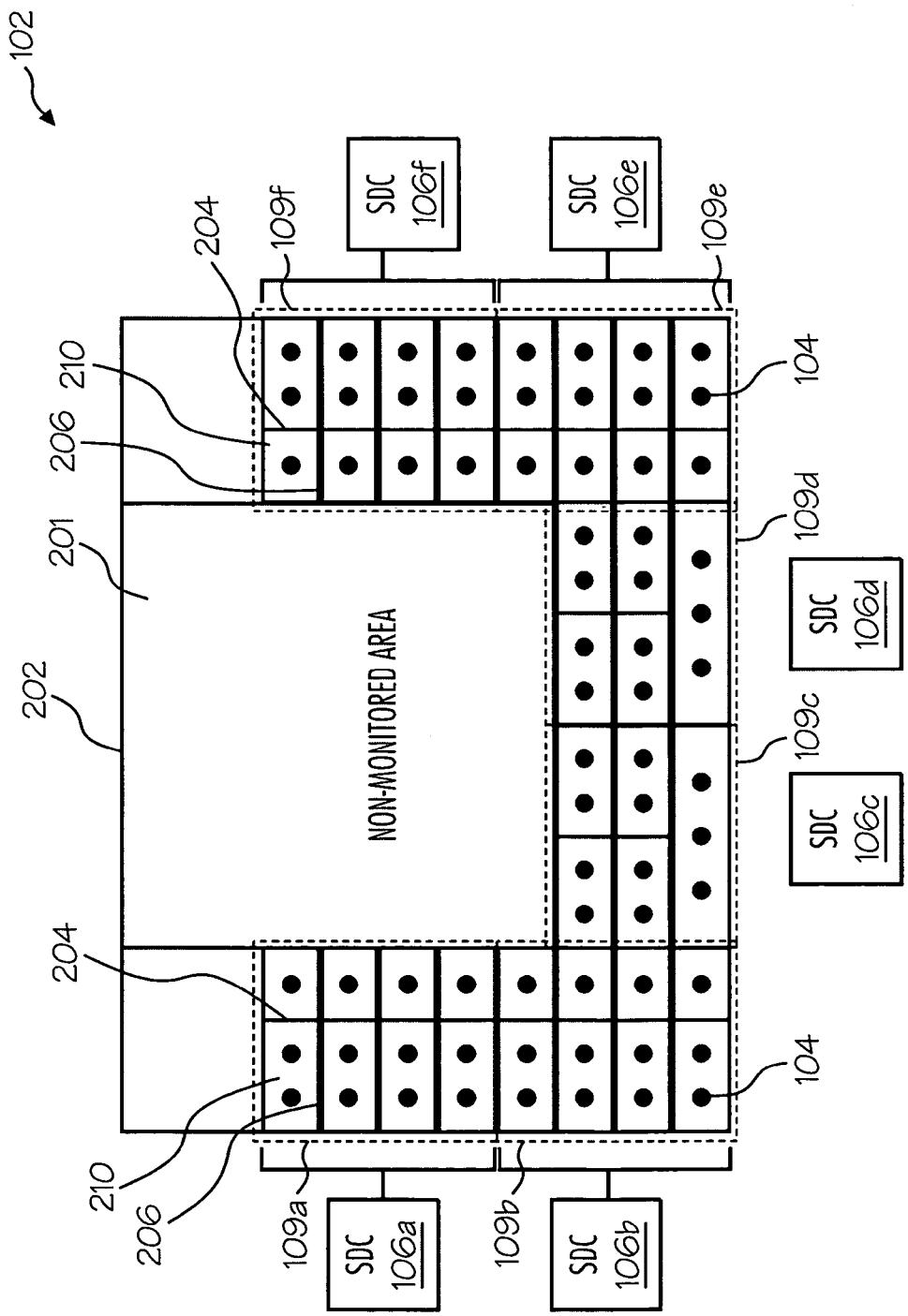
FIG. 2 illustrates the placement of sensors on a monitored, and around a non-monitored section of an aircraft in accordance with the teachings of the present invention.

An exemplary arrangement of the sensors 104 and SDCs 106 in a structural health management system 100 is illustrated in FIG. 2. To avoid unnecessarily complicating FIG. 2, SDCs 106 are illustrated as associated with a grouping of sensors 104 in FIG. 2. As better viewed in FIG. 1, each sensor 104 will be coupled to at least one SDC 106. FIG. 2 illustrates an exemplary section of structure 102 to be tested. As shown in FIG. 2, one or more sensors 104 are placed on the inside surface 202 of the structure 102 in sections 210 bordered by a pair of stringer members 206 and a pair of frame members 204. In the embodiment of FIG. 2, the structure 102 is adjacent to a non-monitored area 201. Non-monitored area 201 can be any area not monitored by the system 100 and, in an avionics embodiment where the structure 102 is aircraft skin, the non-monitored area 201 can be a structure such as a window, door, or the like. As noted, FIG. 2 illustrates the inside surface 202 of the structure 102; the outside of the structure 102 is not visible in this perspective.

In operation, each sensor 104 can produce, transmit and receive elastic wave energy. The elastic wave energy, which is produced by sensor 104 converting mechanical energy to an elastic wave, can manifest itself in a variety of forms such as transient Lamb waves, bulk waves, Rayleigh waves and the like. These elastic waves can be transmitted, reflected, refracted, mode converted and attenuated as the elastic waves propagate through out the structure, interacting with internal features. In one embodiment, the elastic waves, such as Lamb waves, propagate throughout the entire thickness of plate-like structures, such as the composite material used for the skin of an aircraft. As discussed previously, defect characteristics can be determined, in part, from the time-of-flight, signal amplitude, and signal energy (area under the rectified voltage curve) of the propagated elastic waves received by a sensor 104. Additionally, the time-of-flight between sensors 104 or between the start of an elastic wave and its return from reflection of a boundary can be used to determine distances between sensors 104 and between sensors 104 and boundaries.

As discussed previously, it is desirable to verify that the structural health management system 100 is operating correctly and accurately. Pursuant to this objective, all tests and inspection equipment used to determine the airworthiness of articles are calibrated to certification standards acceptable to regulatory agencies such as the FAA. One method of calibration is to measure and compare the operation of test equipment against a known standard or reference. Within certain limits, the operation of the equipment can be adjusted to account for instrumentation drift and variability through comparison with the reference standard. This step in the procedure is referred to herein as calibration-in. After gathering the calibration-in data, the equipment is then used to measure the unknown sample. After the data from testing an unknown sample is collected, the equipment is then again used to measure a known sample. This is referred to herein as the calibration-out procedure and the data collected is known as calibration-out data. If the calibration-in data and calibration-out data match to within a predetermined threshold, it is assumed that the test equipment was working properly when it tested the unknown sample.

In the depicted structural health management system 100, the sensors 104 are permanently mounted on the test material or structure 102. The structure 102 represents both the unknown sample, since the structure can undergo changes due to damage in unknown ways, and the known sample, since the structural health management system 100 is calibrated using the structure to which it is mounted. Thus, the present invention uses the structure 102 and sections of the structure 102 in the calibration process.

Figure 3:
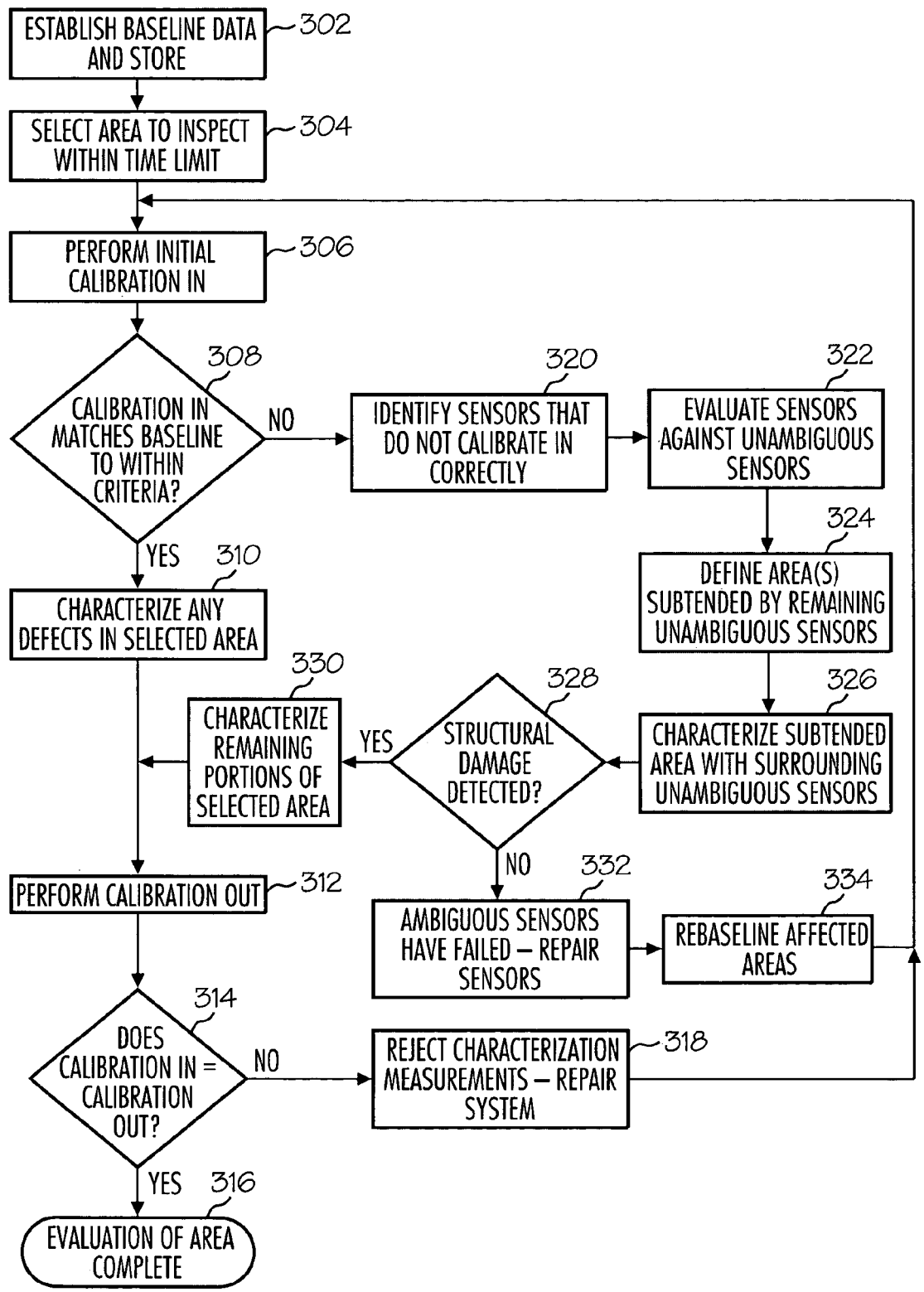
FIG. 3 is a flowchart illustrating an exemplary method for satisfying the certification requirements and verifying the integrity of a structural health management system.

An exemplary method for verifying the integrity of a structural health management system is outlined in the flowchart of FIG. 3. In a first step, step 302, a baseline system measurement is taken shortly after system installation or a repair activity. In one embodiment, each sensor 104 interrogates its local surroundings. This is done by electrically stimulating each sensor 104 to transmit an elastic wave signal that interacts with the boundaries, other sensors 104, and the structure 102. After the short period in which the sensors 104 are being stimulated, the sensors 104, act as receivers to sense the return signals. In one embodiment, this process is known as pulse echo measurements. The signals are collected and then processed attributes of the signals, or the signals themselves are stored for use as a baseline data set.

In one embodiment, a first sensor 104 is pulsed and the transmitted elastic wave is received by surrounding sensors 104. Each receiving sensor 104 can record the time that it receives the elastic wave with respect to the time that the elastic wave was transmitted. From this information a time-of-flight between the transmitting sensor 104 and each of the surrounding sensors 104 can be determined. The lowest time-of-flight typically corresponds to the nearest neighbor to the transmitting sensor 104. The time-of-flight for each sensor 104 and its neighbors can be generated and saved. The nearest neighbor calculation is typically done at installation. The nearest neighbor measurement can also be used for installation testing and sensor 104 location estimation. A method and system for using nearest neighbor measurements for installation testing and sensor 104 location estimation is disclosed in the commonly assigned copending application entitled "Structural Health Management System And Method For Enhancing Availability And Integrity In The Structural Health Management System", having an U.S. application Ser. No. 10/976725, filed on Oct. 29, 2004, and which is hereby incorporated by reference.

As discussed previously, the first step, step 302, is typically done upon initial system installation or after a repair to provide baseline information that can be used in the future. The following steps are typically executed each time the system is used. In step 304, an area of the structure 102 to inspect is selected that can be evaluated according to the process described in FIG. 3 within the time limits necessary to achieve the required levels of functional integrity for the system. If the time between the calibration-in and calibration-out steps is sufficiently small, it can be shown that the probability of system failure during the intervening period of time satisfy functional integrity requirements.

In step 306 a calibration-in procedure is initiated. In the calibration-in procedure, each sensor 104 is electrically stimulated to transmit an elastic wave signal that will interact with the surrounding structures and form a return signal. The return signal is received by sensor 104 and processed attributes of the signal, or the signal themselves, are stored as a calibration-in and calibration-out data set. This is done for every sensor 104 in the selected area.

Next, in step 308, it is determined if the calibration-in data set matched the baseline data set to within predetermined criteria. If the calibration-in data set and the baseline data set match, then the system 100 is assumed to be in the same condition as when the baseline data set was taken and, therefore, is operating correctly. The predetermined criteria can be set such that variations due to environmental factors or other reasons not attributable to an anomalous event can be tolerated. Next, data can be collected using the sensors 104 in step 310 in a characterization process. The characterization process can be any of a number of procedures that provides information concerning the damage state, or health of the structure 102.

After the characterization procedure is completed, a calibration-out procedure is performed in step 312. The calibration-out procedure is typically performed in the same fashion as the calibration-in procedure. The calibration-out procedure generates a calibration-out data set.

Next, it is determined if the calibration-in data set matches the calibration-out data set, step 314. If the calibration-in and calibration-out data sets match, then it is assumed that the structural health management system 100 is working and was working during the characterization process and the procedure ends at step 316. If the calibration-in and calibration-out data sets do not match, then, in step 318, it is assumed that the structural health management system is not operating properly and repairs may be needed. In addition, the characterization measurements previously acquired in step 310, are rejected and any the process returns to step 306.

If, in step 308, it is determined that the calibration-in data set collected in step 306 does not match the baseline data set collected in step 302; an ambiguity exists. Failure of the calibration-in procedure can be due to local structural damage 102, as sensed by the sensors 104, or due to an inoperable sensor 104. One way the sensors 104 can become inoperable is if the sensors 104 have become debonded from the structure 102. The first step in resolving the ambiguity is to identify the sensors that do not calibrate-in correctly (step 320). Then, these sensors are evaluated against neighboring sensors, which are not ambiguous e.g., sensors that calibrated in correctly, in step 322. In one exemplary embodiment, for each potentially inoperable sensor, the neighboring sensors are pulsed and the corresponding time-of-flights between the neighboring sensors and the potentially inoperable sensor are determined. The time-of-flight data are compared to the original time-of-flight data, in step 322. If any number of time-of-flight measurements between a neighboring sensor and the potentially inoperable sensor matches the originally collected time-of-flight measurement between the two sensors, then the potentially inoperable sensor is considered to be operable. These operable sensors then become part of the unambiguous sensor set.

Next, in step 324, areas subtended by the remaining ambiguous sensors are identified. These regions are characterized using all the pertinent, surrounding unambiguous sensors established in step 322. Provided any necessary sensor density requirements are met, the data collected can be evaluated to characterize damage in step 326 to these areas of the structure 102. The method used to estimate damage can vary. One exemplary method to calculate damage in a structural health management system is through the use of a moving average damage algorithm, which is disclosed in the commonly assigned, copending application entitled "Method For Reducing The Computation Resources Required For Determining Damage In A Structural Health Management System" and having an U.S. application Ser. No. 10/976712, and filed Oct. 29, 2004, which is hereby incorporated by reference. Once the damage is determined, remedial methods are determined.

In step 328 it is determined if, according to the damage estimation algorithm(s), any structural damage has occurred. If structural damage has occurred, in step 330, the remaining portions of the selected area is characterized. Then the calibration-out procedure is performed in step 312 and the logic continues according to the previous discussion.

If, according to the damage estimation algorithm, structural damage has not occurred, in step 332 the ambiguous sensors are labeled as inoperable sensors and are subject to a subsequent a repair activity.

Once the sensors have been repaired and independently validated, the affected structural area is rebaselined in step 334. Rebaselining, in one exemplary embodiment, can be done in the same manner as the original baseline measurement. Any continuation of the damage assessment after the rebaselining begins again at step 306.

In the preceding methods, when data sets are compared there is allowed some degree of variance that represents the expected differences due environmental issues and experimentation error. Thus a match need not be an exact match between data set but instead can be a match within a certain criteria level, the level set to compensate for environmental issues and experimental errors.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for verifying the integrity of a structural health management system comprising a plurality of sensors mounted on a structure, the method comprising:

establishing a baseline data set for each of the plurality of sensors;

performing a calibration-in procedure to collect a calibration-in data set for each of the plurality of sensors;

comparing the calibration-in data set for each sensor of the plurality of sensors to the baseline data set for each sensor of the plurality of sensors; and if the calibration-in data set and the baseline data set match:

performing a structural characterization;

performing a calibration-out procedure to generate a calibration-out data set;

verifying that the structural health management system is working by comparing the calibration-out data set and the calibration-in data set for each sensor of the plurality of sensors; and generating a signal indicating the structural health management system is working, if the calibration-out data set and the calibration-in data set match.

2. The method of claim 1 further comprising performing the calibration-in procedure and the calibration-out procedure within a predetermined time limit.

3. The method of claim 2 wherein the step of performing a calibration-in procedure further comprises performing a calibration-in procedure on a subset of the plurality of sensors, the subset chosen based on fulfilling the predetermined time limit.

4. The method of claim 1 wherein the step of establishing a baseline data set for each of the plurality of sensors further comprises generating an electrically stimulated elastic wave at each of the plurality of sensors and storing information from a return pulse.

5. The method of claim 1 further comprising, if the calibration-in data set does not match the baseline data set, the steps of:
identifying non-matching sensors of the plurality of sensors whose calibration-in data does not match its baseline data set;
evaluating each of the non-matching sensors against neighboring sensors to determine a set of ambiguous sensors;
identifying one or more areas surrounded by the set of ambiguous sensors; and
characterizing the one or more areas surrounded by the set of ambiguous sensors.

6. The method of claim 5 further comprising
if the characterization fails to detect any damage:
identifying the ambiguous sensors as failed sensors;
establishing a new baseline data set for areas containing damaged sensors after repair; and
if the characterization detects any damage:
considering the previously ambiguous sensors as working;
characterizing any remaining uncharacterized area; and
performing a calibration-out procedure.

7. The method of claim 5 wherein the step of evaluating each of the non-matching sensors further comprises:
determining a time-of-flight between each of the non-matching sensors and the neighboring sensors associated with each of the sensors; and
comparing the time-of-flight with a baseline time-of-flight.

8. The method of claim 7 wherein the step of establishing a baseline time-of-flight further comprises electrically stimulating each sensor of the plurality of sensors and ordering the neighboring sensors pairs from the plurality of sensors using the time-of-flight measurements associated with the received electrically stimulated mechanical pulses.

9. The method of claim 8 further comprising determining that the structural health managements system is damaged if the calibration-out data set fails to match the calibration-in data set.

10. A method for verifying the integrity of a structural health management system mounted on a structure comprising:
(a) performing a calibration-in procedure on the structural health management system using a previous assessment of the structure as a reference and generating a calibration-in data set from the calibration-in procedure;
(b) interrogating the structure to determine if there is damage, the structure treated as an unknown;
(c) performing a calibration-out procedure on the structural health management system using the previous assessment of the structure as a reference and generating a calibration-out data set from the calibration-out procedure;
(d) comparing the calibration-in data set with the calibration-out data set; and
(e) generating a signal indicating the structural health management system is working, if the calibration-in data set matches the calibration-out data set.

11. The method of claim 10 further comprising performing the steps (a) to (c) within a predetermined time limit.

12. The method of claim 10 wherein the step of performing a calibration-in further comprises:
establishing a baseline data set by performing a baseline assessment;
performing a calibration-in procedure to generate the calibration-in data set;
comparing the calibration-in data set to the baseline data set;
if the calibration-in data set and the baseline data set match, executing step (b).

13. The method of claim 12 wherein the step of performing a calibration-in procedure further comprises performing a calibration-in procedure on a portion of the structure, the portion of the structure chosen based on fulfilling the predetermined time limit.

14. The method of claim 12 further comprising, if the calibration-in data set does not match the baseline data set, the steps of:
identifying non-matching sensors of the plurality of sensors whose calibration-in data does not match the baseline data set;
evaluating each of the non-matching sensors against neighboring sensors to determine a set of ambiguous sensors; and
characterizing areas surrounded by the set of ambiguous sensors.

15. The method of claim 12 wherein the step of establishing a baseline data set for each of the plurality of sensors further comprises generating a mechanical elastic wave pulse at each of the plurality of sensors and storing information from a return pulse.

16. The method of claim 14 wherein the step of evaluating each of the non-matching sensors further comprises:
determining a time-of-flight between each of the non-matching sensors and the neighboring sensors associated with each of the sensors; and
comparing the time-of-flight with a baseline time-of-flight.

17. The method of claim 16 wherein the step of establishing a baseline time-of-flight further comprises generating an elastic wave from each of the plurality of sensors and selecting as neighboring sensors those sensor from the plurality of sensors that receive the pulse with the smallest time of flight in a ranked order.

18. The method of claim 14 further comprising
if the step of characterizing detects any damage:
identifying the ambiguous sensors as failed sensors;
rebaseline areas containing damaged sensors; and
if the characterization fails to detect any damage:
characterize any remaining uncharacterized area; and
performing a calibration-out procedure.

19. A structural health management system comprising:
a plurality of sensors mounted on a to-be-tested structure,
one or more processors coupled to each of the sensors and configured to:
establish a baseline data set for each of the plurality of sensors;

perform a calibration-in procedure to collect a calibration-in data set for each of the plurality of sensors;
compare the calibration-in data set for each sensor of the plurality of sensors to the baseline data set for each sensor of the plurality of sensors;
if the calibration-in data set and the baseline data set match:
    perform a structural characterization;
    perform a calibration-out procedure to generate a calibration-out data set; and
    verify that the structural health management system is working by comparing the calibration-out data set and the calibration-in data set and achieving a match for each of the plurality of sensors;
if the calibration-in data set does not match the baseline data set:
    identify non-matching sensors of the plurality of sensors whose calibration-in data does not match the baseline data set;
    evaluate each of the non-matching sensors against neighboring sensors to determine a set of ambiguous sensors;
    identify areas surrounded by the set of ambiguous sensors
    characterize the areas surrounded by the set of ambiguous sensors; and
    if the characterization fails to detect any damage:
        identify the ambiguous sensors as failed sensors;
        rebaseline areas containing damaged sensors; and
    if the characterization detects any damage:
        characterize any remaining uncharacterized area; and
        perform a calibration-out procedure.

20. The system of claim 19 further comprising performing the calibration-in procedure and the calibration-out procedure within a predetermined time limit.

* * * * *